(12) United States Patent
Mozdy

(10) Patent No.: US 7,136,550 B2
(45) Date of Patent: Nov. 14, 2006

(54) SINGLE-FIBER LAUNCH/RECEIVE SYSTEM FOR BIOSENSING APPLICATIONS

(75) Inventor: Eric J. Mozdy, Elmira, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 10/977,520

(22) Filed: Oct. 28, 2004

(65) Prior Publication Data
US 2006/0093254 A1 May 4, 2006

(51) Int. Cl.
G02B 6/00 (2006.01)
G02B 6/26 (2006.01)
G02B 6/42 (2006.01)

(52) U.S. Cl. .............................. 385/28; 385/29; 385/12
(58) Field of Classification Search ................. 385/12, 385/13, 37, 27–29
See application file for complete search history.

(56) References Cited

U.S. PATENT DOCUMENTS

| | | | |
|---|---|---|---|
| 5,696,863 A * | 12/1997 | Kleinerman | 385/123 |
| 5,712,937 A * | 1/1998 | Asawa et al. | 385/12 |
| 6,185,346 B1 * | 2/2001 | Asawa et al. | 385/28 |
| 6,487,338 B1 * | 11/2002 | Asawa et al. | 385/29 |
| 6,597,820 B1 | 7/2003 | Sheem | 385/12 |
| 6,621,947 B1 * | 9/2003 | Tapanes et al. | 385/12 |
| 6,937,151 B1 * | 8/2005 | Tapanes | 340/550 |
| 2002/0126954 A1 * | 9/2002 | Aswawa et al. | 385/28 |
| 2002/0127565 A1 | 9/2002 | Cunningham et al. | 435/6 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2003/0126930 A1 | 7/2003 | DeLaPuente et al. | 73/800 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0223881 A1 | 11/2004 | Cunningham et al. | 422/82.05 |
| 2005/0213868 A1 * | 9/2005 | Cunningham | 385/12 |
| 2006/0029322 A1 * | 2/2006 | Mihailov et al. | 385/12 |

FOREIGN PATENT DOCUMENTS

EP  1 089 062  4/2001

(Continued)

OTHER PUBLICATIONS

A. Brandenburg et al., "Grating Coupler As Chemical Sensors: A New Optical Configuration", Sensor and Actuators B, vol. 17, 1993, pp. 35-40.

(Continued)

*Primary Examiner*—Brian Healy
*Assistant Examiner*—Charlie Peng
(74) *Attorney, Agent, or Firm*—Thomas R. Beall; William J. Tucker

(57) ABSTRACT

An interrogation system and method are described herein which use a single-fiber launch/receive system for interrogating a biosensor (optical sensor) to detect the occurrence of a bio-chemical interaction (e.g., biological binding of ligands with analytes). In one embodiment, the single-fiber launch/receive system utilizes a multimode fiber to help interrogate the biosensor. In another embodiment, the single-fiber launch/receive system utilizes a downjacketed singlemode fiber to help interrogate the biosensor.

27 Claims, 3 Drawing Sheets

FOREIGN PATENT DOCUMENTS

| JP | 07-260617 | 10/1995 |
| JP | 08-201196 | 8/1996 |
| JP | 09-152308 | 6/1997 |

OTHER PUBLICATIONS

B. Cunningham et al., "Colorimetric Resonant Reflection As A Direct Biochemical Assay Technique", Sensors and Actuators B, vol. 81, 2002, pp. 316-328.

N.H. Fontaine et al., Variable-Angle Internal-Reflection Raman Spectroscopy For Depth-Resolved Vibrational Characterization Of Polymer Thin Films, Physical Review B, vol. 57, No. 7, Feb. 15, 1998, pp. 3807-3810.

K. Tiefenthaler et al., "Sensitivity Of Granting Couplers As Integrated-Optical Chemical Sensors", Journal Opt. Soc. Am. B., vol. 6, No. 2, Feb. 1989, pp. 209-220.

* cited by examiner

SINGLE-FIBER LAUNCH/RECEIVE SYSTEM FOR BIOSENSING APPLICATIONS

BACKGROUND OF THE INVENTION

1. Field of the Invention

The present invention relates in general to optical non-contact sensor technology and more particularly to an interrogation system which uses a single-fiber launch/receive system for interrogating a biosensor to detect the occurrence of a bio-chemical interaction (e.g., biological binding of ligands with analytes).

2. Description of Related Art

Many areas of biological research today utilize optical non-contact sensor technology to help perform increasingly sensitive and time-constrained assays. In such assays, an optical interrogation system can be used to monitor changes in the refractive index or variations in the optical response of an optical sensor (biosensor) as a biological substance is brought into a sensing region of the optical sensor. The presence of the biological substance alters the optical response of the optical sensor when it causes a bio-chemical interaction like material binding, adsorption etc . . . This alteration of the optical response enables one to use the optical sensor to directly monitor biological events in label-free assays where the expense and experimental perturbations of fluorescent dyes are completely avoided.

Inherent in this type of optical interrogation system is the need to use a launch/receive system to launch the light that interacts with the optical sensor, and to subsequently receive the output of the optical sensor to enable the interpretation of the sensor's response. While a launch/receive system that utilizes free-space optics provides the most direct control of the optical signals, the launch/receive system that utilizes optical fiber has many desirable properties. For example, the launch/receive system that uses optical fiber is immune to dust and dirt, does not need to use many expensive bulk optical components, and has the ability to create an arbitrary light path which allows complete flexibility in the location of the light source, the optical sensor, and the light detector.

However, one of the main drawbacks of a launch/receive system that uses optical fiber is the difficulty and poor efficiency of coupling light into the fiber core. For instance in the case of optical sensors, coupling must generally occur at two different places: the light source and the sensor output. At the light source, the problem is usually mitigated by the availability of prepackaged optical fiber light sources. But, the sensor output poses a much more challenging task. Unless specifically integrated into the optical fiber, the typical optical sensor does not have the cylindrical geometry necessary to output a mode similar to the target waveguide of the optical fiber. As such, the coupling efficiency from the optical sensor into the fiber is poor, and large-area multimode fibers are sometimes employed to alleviate this problem. Furthermore, the sensor often has input and output ports that are spatially separated, or at least not completely coincident in space (slightly different coupling angle or location). This means that the launch fiber is often precluded from being the receive fiber, even if the loss from coupling back into a singlemode fiber is tolerable. Thus, the traditional launch/receive system typically requires the use of two fibers (one each for the launch and receive functions), and furthermore may require two different types of fiber: multimode at the receive end for maximum light collection, and singlemode at the launch end in order to have well-defined, consistent operation of the optical sensor. As an example, consider a grating-coupled waveguide (GCW) optical sensor, described in many places in the literature such as in an article by K. Tiefenthaler et al. entitled "Sensitivity of Grating Couplers as Integrated-Optical Chemical Sensors", J. Opt. Soc. Am. B 6, 209–220 (1988). It is well known that the GCW optical sensor requires a light beam with a well-defined, single-longitudinal mode spatial profile as an input, while the output mode of the GCW optical sensor is less powerful, not spatially well-defined, emerges at a complimentary angle to the input beam, and is often spatially shifted from the input beam. Not surprisingly, the literature references that employ optical fiber as the GCW optical sensor interface describe the use of two separate fibers (or at least fiber cores, packaged into the same cladding or jacket) to provide for the dual launch/receive functionality. For example, see the article by B. Cunningham, P. Li, B. Lin, and J. Pepper, "Colorimetric Resonant Reflection as a Direct Biochemical Assay Technique", Sensors and Actuators B 81, 316–328 (2002). The contents of this article and the previous article are incorporated by reference herein.

Unfortunately, since the traditional multiple-fiber launch/receive system requires two separate optical fibers it also has a lot of complexity due to the sensitive alignment of the two optical fibers or the manufacture of specialized integrated optical devices such as gradient index (GRIN) lens collimators, fiber alignment chucks, or fused/lensed fiber systems. Accordingly, there is a need for a single-fiber launch/receive system that can address the aforementioned shortcomings and other shortcomings of the traditional multiple-fiber launch/receive system. These needs and other needs are satisfied by the single-fiber launch/receive system of the present invention.

BRIEF DESCRIPTION OF THE INVENTION

The present invention includes an interrogation system and method which uses a single-fiber launch/system for interrogating a biosensor (optical sensor) to detect the occurrence of a bio-chemical interaction (e.g., biological binding of ligands to analytes). In one embodiment, the single-fiber launch/receive system utilizes a multimode fiber to help interrogate the biosensor. In another embodiment, the single-fiber launch/receive system utilizes a downjacketed singlemode fiber to help interrogate the biosensor.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

Figure 1:
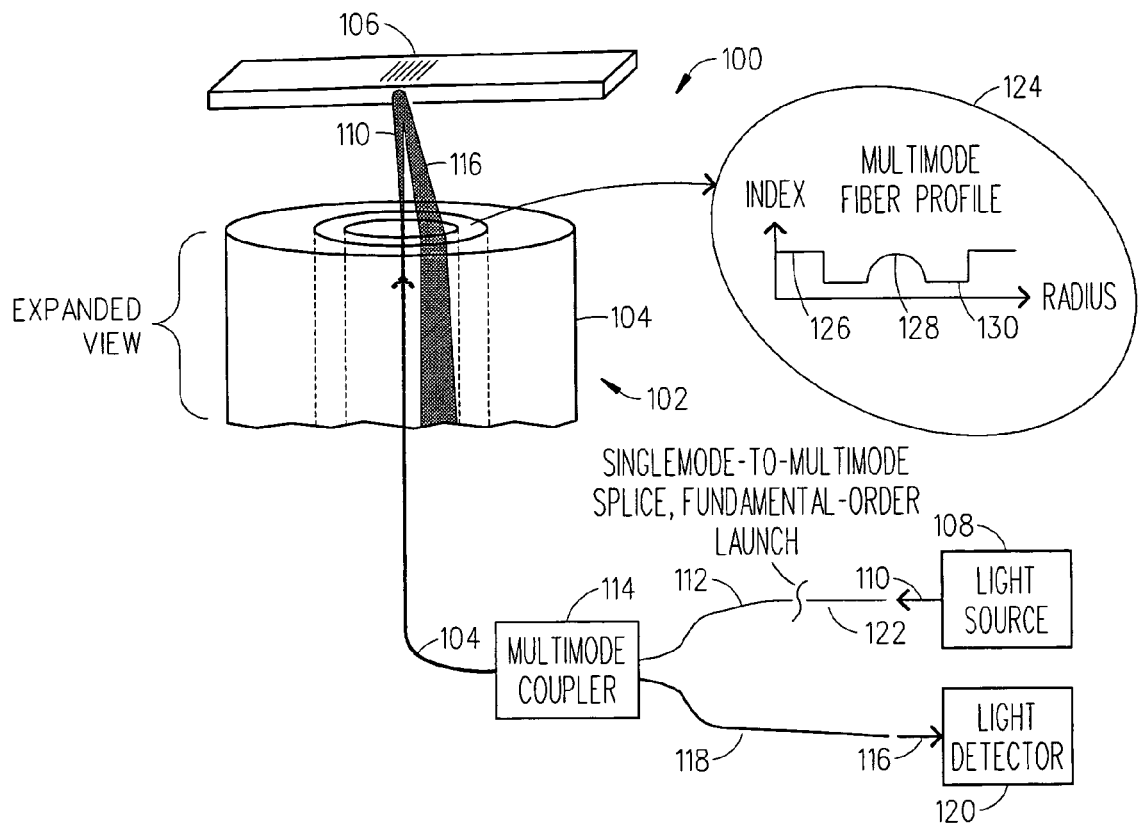
FIG. 1 is a diagram that illustrates an interrogation system which includes a single-fiber launch/receive system that uses a multimode fiber to interrogate a biosensor in accordance with a first embodiment of the present invention.

Referring to FIG. 1, there is a diagram that illustrates an interrogation system 100 which includes a single-fiber launch/receive system 102 that uses a multimode fiber 104 (preferably graded-index multimode fiber) to interface with a biosensor 106 to detect the occurrence of a bio-chemical interaction (e.g., biological binding of ligands to analytes) on top of the biosensor 106. As shown, the interrogation system 100 includes a light source 108 (e.g., SLED, laser, etc. 108) that outputs a light beam 110 into a fiber optic cable 122 (e.g., singlemode fiber optic cable 122). This fiber is spliced to a graded-index multimode fiber cable 112, which under the proper alignment couples the single-mode beam 110 from the cable 122 into the fundamental (lowest-order) mode of the multimode fiber cable 112, thereby preserving the "single-modeness" of the source. While graded-index fiber 112 is preferable as it easily preserves the fundamental mode propagation in the absence of microbending, anyone skilled in the art would understand that any multimode fiber capable of preserving a fundamental mode along its length could be used in the system 100. The light 110 then passes through a 3 dB coupler 114 (e.g., splitter/combiner 114) which is generally produced from the same graded-index multimode fiber as the launch/receive fiber 104 nearest the biosensor 106. Alternately, this coupler 114 can be a combination of fiber and free-space optics (e.g. fiber collimators and beamsplitter), similar to many systems commercially offered today, provided the coupler 114 preserves the optical modes propagating in either direction. After passing through the coupler 114, the single-mode source light 110 enters the graded-index multimode fiber 104 which emits the light 110 as a single-spatial mode sensor input beam 110 to the biosensor 106 (e.g., GCW biosensor 106). The biosensor 106 then directs a sensor output beam 116 back into the graded-index multimode fiber 104. Due to the shape of the sensor output beam 116, the return light will couple into multiple modes of the fiber 104 for the return path, and thereby be characterized by multimode propagation, contrary to the counter-propagating (single-mode) source light 110. This sensor output light 116 then passes through the 3 dB coupler 114 into a fiber optic cable 118 (e.g., multimode fiber optic cable 118) which directs the light 116 to a light detector 120 (e.g., photodiode, spectrograph, CCD camera . . . ). A computer or other electrical hardware (not shown) which is connected to the light detector 120 is then used to analyze the sensor output beam 116 to determine whether or not there was a biochemical interaction (e.g., biological binding of ligand to analyte) on top of the biosensor 106.

In particular, the single-fiber launch/receive system 102 interfaces with the biosensor 106 using a single fiber 104 (graded-index multimode fiber 104) where the multimode fiber 104 is able to output a sensor input beam 110 to the biosensor 106 after a single transverse (fundamental) mode therein is excited to generate the light for the sensor input beam 110. And, the multimode fiber 104 is able to receive a sensor output beam 116 from the biosensor 106 by using a collection of modes therein to collect the light from the sensor output beam 116. A detailed description is provided next about the functionality, structure, and mode-coupling associated with the multimode fiber 104.

The multimode fiber 104 (preferably graded-index fiber) utilizes different modes including the fundamental mode in the forward (launch) direction of propagation to emit the sensor input beam 110 and a collection of modes in the backward (receive) direction of propagation to receive the sensor output beam 116. The forward (launch) mode preferably embodies a single transverse mode (the fundamental, or lowest-order mode) of the multimode fiber 104, while the backward (receive) mode preferably involves a collection of modes typical of multimode operation, embodying maximal spatial overlap with the optical output of the biosensor 106. The multimode fiber 104 must have the property that it preserves the fundamental mode upon propagation along its length; in other words, there must be minimal mode-coupling during propagation. In this manner, the excellent spatial properties of single mode operation apply to the launch of the sensor output beam 110, while the large collection efficiency (numerical aperture) of a multimode fiber can be advantageously utilized at the receive end to receive the sensor output beam 116.

As an example, the inset 124 shows a typical index of refraction profile for the graded-index multimode fiber 104 and 112 used throughout the system 100, where numeral "128" is the graded-index core, "130" is the cladding, and "126" is the polymer (typically acrylate) jacket protecting the glass fiber. The fundamental mode of the graded-index multimode fiber 112 (and subsequently, fiber 104) can be excited by splicing a smaller-core singlemode fiber 122 to the multimode fiber 112. For instance, the multimode fiber 112 can typically contain a >50 µm core diameter which allows a much larger collection area than a ≦10 µm singlemode fiber core in the single mode fiber 122. The multimode coupler 114 is also important in this scheme, as it needs to employ multimode fiber that is nearly identical to the multimode fibers 112 and 104 in order to preserve both the fundamental mode launch of fiber 112 as well as the multimode sensor output light returning from fiber 104. Alternately, a beamsplitter/lens assembly can be used to provide the functionality of the coupler 114. In this way, the multimode fiber 104 can be employed where only the lowest-order (fundamental) mode is excited on the launch end, while the entire multimode core is used at the receive end. The excitation of only the fundamental mode to generate the sensor output beam 110 can be accomplished by a restricted-mode launch.

Figure 2A:
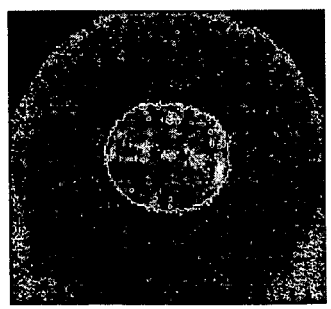
FIGS. 2A and 2B are two photos illustrating a normal multimode launch (FIG. 2A) and an innovative fundamental mode launch within a multimode fiber (FIG. 2B) obtained during an experiment using the multimode fiber of the single-fiber launch/receive system shown in FIG. 1.
Figure 2B:
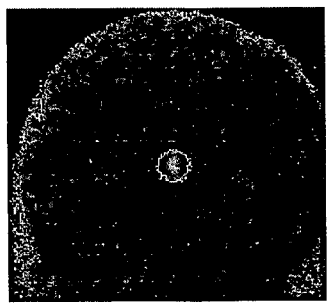

To demonstrate the innovative concept of a restricted mode launch using a graded-index multimode fiber 104, the inventor performed some tests. In these tests, a single mode fiber 122 (e.g., Corning Puremode® PM 480 at the test wavelength of 633 nm) was spliced to a multimode fiber 112 (e.g., Corning Infinicore® 600) after the fiber cores were aligned so as to launch only the fundamental mode. FIGS. 2A and 2B, are photos that show for two cases the resulting mode exiting the graded-index multimode fiber 104 where one case shows a normal multimode launch (see FIG. 2A) and the other case shows the innovative single mode launch (see FIG. 2B). FIG. 2B demonstrates the ability to have a well-defined, single mode exit the graded-index multimode fiber 104 while retaining the ability to utilize a very large core area for collection.

Figure 3:
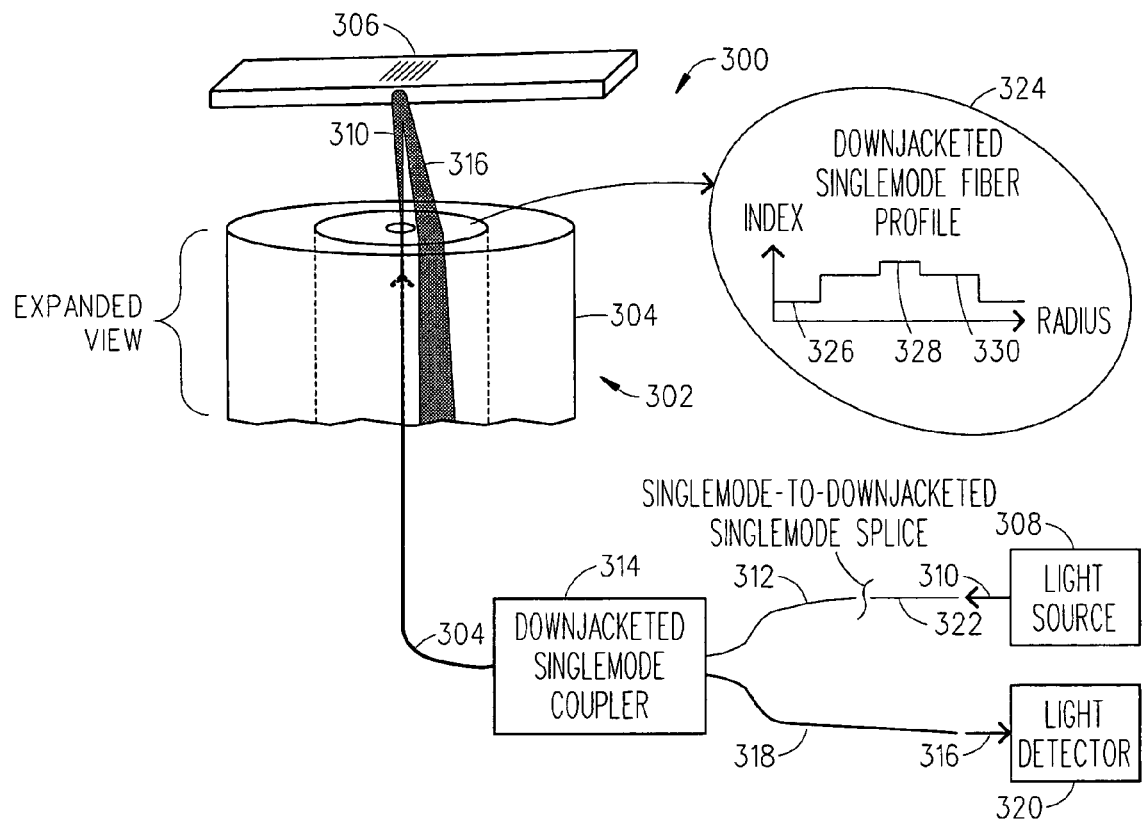
FIG. 3 is a diagram that illustrates an interrogation system which includes a single-fiber launch/receive system that uses a downjacketed singlemode fiber to interrogate a biosensor in accordance with a second embodiment of the present invention.

Referring to FIG. 3, there is a diagram that illustrates an interrogation system 300 which includes a single-fiber launch/receive system 302 that uses a downjacketed, singlemode fiber 304 to interface with a biosensor 306 to detect the occurrence of a bio-chemical interaction (e.g., biological binding of ligands with analytes) on top of the biosensor 306. As shown, the interrogation system 300 includes a light source 308 (e.g., SLED, LED, laser . . . ) that outputs a light beam 310 into the core of a fiber optic cable 322 which passes through a 3 dB coupler 314 (e.g., downjacketed singlemode fiber coupler 314, or free-space splitter/combiner 314) and enters the downjacketed singlemode fiber 304 which emits the light 310 as a sensor input beam 310 to the biosensor 306 (e.g., GCW biosensor 306). The biosensor 306 then directs a sensor output beam 316 into the cladding of the downjacketed singlemode fiber 304 which passes the light 316 through the 3 dB coupler 314 into a downjacketed singlemode fiber optic cable 318 which directs the light 316 to a light detector 320 (e.g., photodiode, spectrograph, CCD camera . . . ). A computer or electrical hardware (not shown) which is connected to the light detector 320 is then used to analyze the sensor output beam 316 to determine whether or not there was a bio-chemical interaction (e.g., biological binding of ligand to analyte) on top of the biosensor 306.

In particular, the single-fiber launch/receive system 302 interfaces with the biosensor 306 using a single fiber 304 (downjacketed singlemode fiber 304) where the downjacketed singlemode fiber 304 is able to output a sensor input beam 310 to the biosensor 306 after a single transverse (fundamental) mode therein is excited in the fiber core to generate the light for the sensor input beam 310. And, the downjacketed singlemode fiber 304 is able to receive a sensor output beam 316 from the biosensor 306 by using a collection of modes within the cladding therein to collect the light from the sensor output beam 316. A detailed description is provided next about the functionality, structure, and manufacture of the downjacketed singlemode fiber 304.

The downjacketed singlemode fiber 304 utilizes different modes including the fundamental core mode in the forward (launch) direction of propagation to emit the sensor input beam 310 and a collection of cladding modes in the backward (receive) direction of propagation to receive the sensor output beam 316. The forward (launch) mode preferably embodies a single transverse mode in the core of the singlemode fiber 304, while the backward (receive) mode preferably embodies a collection of cladding modes typical of multimode operation. In this manner, the excellent spatial properties of single mode operation apply to the launch of the sensor output beam 310, while the large collection efficiency (numerical aperture) of a multimode fiber can be advantageously utilized at the receive end to receive the sensor output beam 316.

As an example, the inset 324 shows a typical index of refraction profile for the downjacketed singlemode fiber used throughout the system 300, where numeral "328" is the fiber core, "330" is the cladding, and "326" is the polymer jacket protecting the glass fiber. As the (simple, step-index) index profile shows, the downjacketed singlemode fiber 304 can be made by using a polymer jacket 326 that has a lower index than a fiber cladding 330 which allows the fiber cladding 330 to act as a large-core multimode waveguide for the receive function. This type of downjacketed singlemode fiber 304 is different than traditional singlemode optical fiber which is made with a polymer (typically acrylate) jacket: in the typical case, the jacket of the traditional fiber is designed to have a higher index than the fiber cladding so at to prevent the cladding waveguide (employed in this invention) that would cause troublesome interference in telecommunications networks by capturing and guiding spurious light leaking out of the core in long-distance transmission. As such, the downjacketed singlemode fiber 304 which uses the fiber cladding 330 as a return waveguide is a novel use of ordinary fiber that can be made by making an inexpensive modification to the fiber coating 326. For instance, in one embodiment of the downjacketed singlemode fiber 304, the fiber cladding 330 can have a 125 μm diameter which yields a very large collection area even when compared to traditional telecommunications multimode fibers.

Referring to both embodiments of the single-fiber launch/receive system 102/302, there is a significant advantage that is brought about because of their cylindrical symmetry. It is well known that many optical biological sensors 106/306 are designed with some small angle or displacement between the sensor input beam 110/310 and the sensor output beam 116/316. As a result, the sensor output beam 116/316 is not likely to be collinear with the sensor input beam 110/310, and the input/output beams thereby define a launch/receive axis for the system. In a traditional dual-fiber launch/receive system, the launch and receive fibers must therefore be precisely aligned relative to this sensor input/output axis. This consideration is rendered unnecessary by the single fiber launch/receive system 102/302 described herein because the cylindrical symmetry of the optical fiber 104/304 allows the receipt of the sensor output light 116/316 in any direction relative to the launch; the fiber 104/304 must simply be placed close enough to the biosensor 106/306 to allow collection of the reflected light 116/316. One can easily appreciate this fact by rotating the launch/receive fiber 104/304 in the systems 100/300 of FIGS. 1 and 3: rotation of the fiber 104/304 has no effect on the operation. As a result, the single fiber launch/receive system 102/302 does not need to undergo a complicated and expensive procedure to align the launch/receive axis as is required in the traditional dual fiber launch/receive system.

It should also be appreciated that both embodiments of the single-fiber launch/receive system 110/310 can utilize beam-shaping optics at the exit facet of the fiber 104/304. For example, if the numerical aperture of the single mode that exits the bare fiber 104/304 is unacceptably large for the design of the biosensor 106/306, a type of lens (ball termination, GRIN, or free-space optic) may be used to better collimate the light beam 110/310. This of course requires that the lens used has a large enough field of view to accept the reflected beam 116/316 so the benefits of the larger core would still be realized on the return path. As such, the single-fiber launch/receive system 110/310 can still utilize separate modal paths in the opposite directions, even if the end of the fiber 104/304 has a special lens or optic between it and the biosensor 106/306.

Figure 4A:
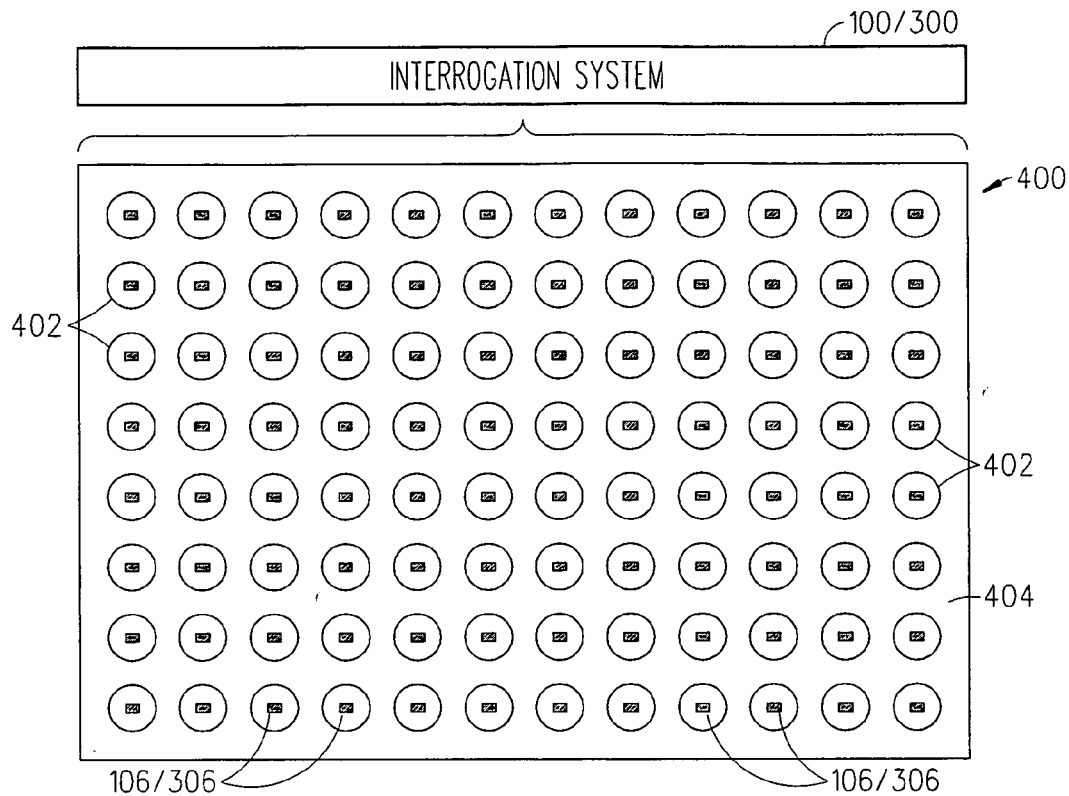
FIGS. 4A and 4B illustrate a top view and cross-sectional side view of a microplate that has wells the bottom of which each incorporate a biosensor that can be interrogated by either of the interrogation systems shown in FIGS. 1 and 3.
Figure 4B:
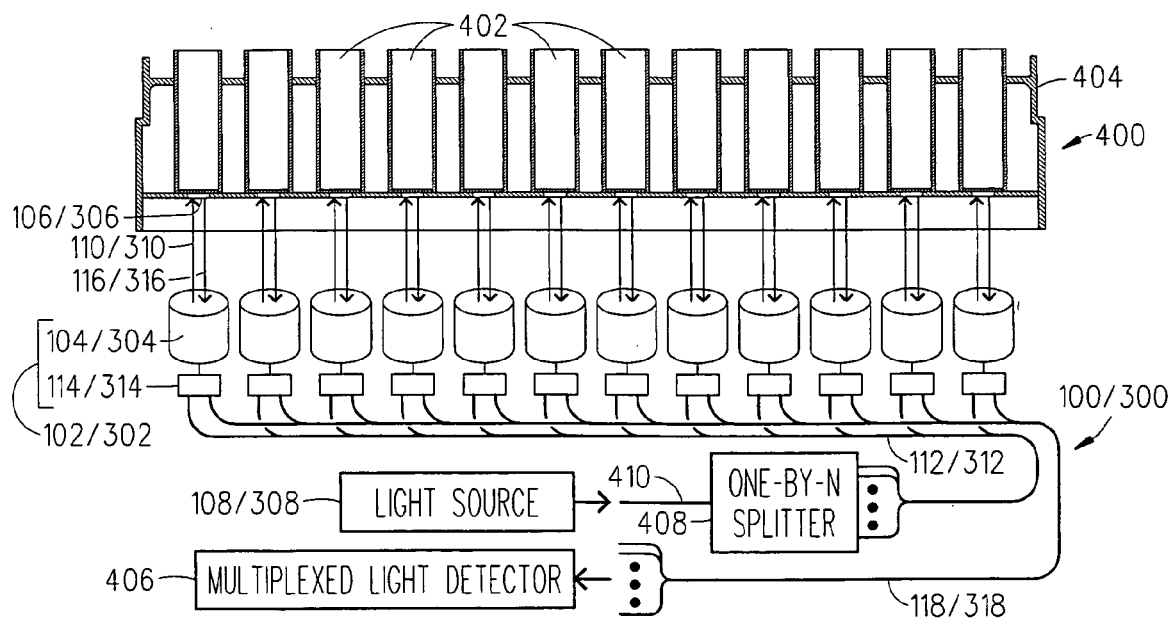

Referring to FIGS. 4A and 4B, there are respectively illustrated a top view and cross-sectional side view of an exemplary microplate 400 that has wells 402 the bottom of which each incorporate a biosensor 106/306 that can be interrogated by an interrogation system 100/300 like the ones shown in FIGS. 1 and 3. In the illustrative example, an array of sensors 106/306 are incorporated within the bottoms of wells 402 formed within a frame 404 of the microplate 400 (e.g., 96-well microplate 400). The interrogation system 100/300 includes a light source 108/308 which emits a beam 410 into a 1-by-N splitter 408 (power equally divided into N singlemode fibers) which is then delivered to the couplers 114/314 and thereby to a series of single fibers 104/304 which subsequently emit an optical beam 110/310 at each sensor 106/306 in each well 402 and receive an optical beam 116/316 from each sensor 106/306 in each well 402. On the return path, the outputs of the couplers 114/313 of each single-fiber launch/receive system 102/302 are gathered together and delivered into a multiplexed light detector 406.

The multiplexed light detector 406 can be many light detectors in parallel, or some other array-based detection element such as a CCD camera, optical multichannel analyzer, etc. A computer or electrical hardware (not shown) which is connected to the multiplexed light detector 406 is then used to analyze the multiple sensor output beams 116/316 to determine whether or not there were bio-chemical interactions (e.g., biological binding of ligands to analytes) on top of the biosensors 106/306. In this way, multiple sensors 106/306 can be interrogated at the same time.

Figure 5:
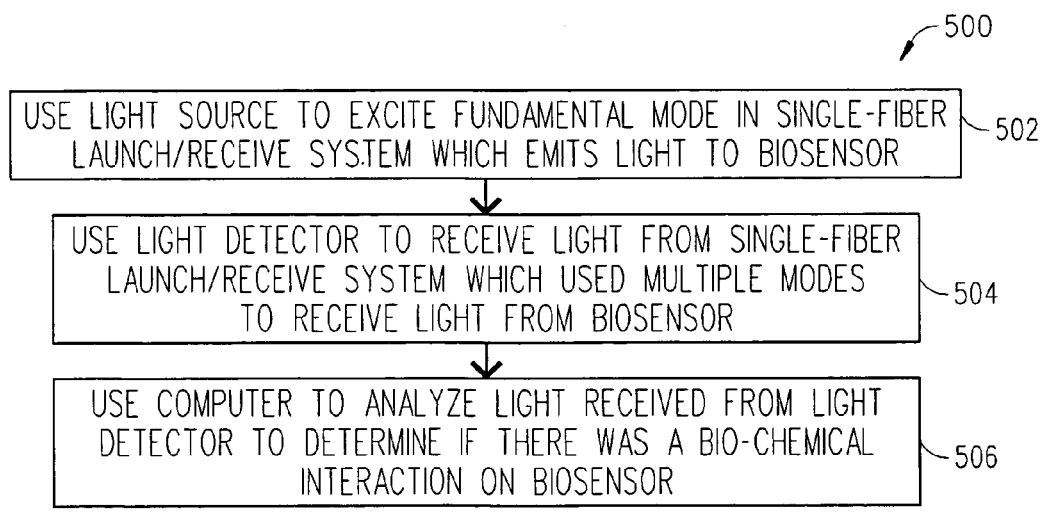
FIG. 5 is a flowchart illustrating the basic steps of a preferred method for interrogating a biosensor using either of the interrogation systems shown in FIGS. 1 and 3 in accordance with the present invention.

Referring to FIG. 5, there is a flowchart illustrating the basic steps of a preferred method 500 for interrogating a biosensor 106/306 using the interrogation system 100/300 in accordance with the present invention. Beginning at step 502, the light source 108/308 is used to excite a single transverse (fundamental) mode in a single fiber 104/304 of the single-fiber launch/receive system 100/300 so as to direct a sensor input beam 110/310 to the biosensor 106/306. At step 504, the light detector 120/320 is used to receive a sensor output beam 116/316 from the single fiber 104/304 in the single-fiber launch/receive system 100/300 which used a plurality of modes to receive the sensor output beam 116/316 from the biosensor 106/306. Then at step 506, a computer or electrical hardware (not shown) which is connected to the light detector 120/320 is used to analyze the sensor output beam 116/316 to determine whether or not there was a bio-chemical interaction (e.g., biological binding of ligands with analytes) on top of the biosensor 106/306.

It should be appreciated that the single-fiber launch/receive system 102/302 can be used to interrogate a biosensor 106/306 so that a computer or electrical hardware can also determine whether or not a biological substance such as a cell, molecule, protein, drug, chemical compound, nucleic acid, peptide or carbohydrate is present on a biosensor 106/306. In addition, the single-fiber launch/receive system 102/302 can be used to help perform other label or label-free studies such as photoluminescence assays, fluorescence assays, scattering assays, absorbance assays, cell migration assays, drug permeability assays, drug solubility studies, virus detection studies and protein secretion studies.

From the foregoing, it can be readily appreciated by those skilled in the art that the single-fiber launch/receive system of the present invention involves a non-traditional use of optical fibers to overcome the added expense and complexity of traditional multiple-fiber launch/receive systems. The single-fiber launch/receive system of the present invention has many possible embodiments, each involving the central concept: utilizing different modes of the same optical fiber in the forward (launch) and backward (receive) directions of propagation. As applied to the GCW optical sensor described above, the forward mode preferably embodies a single transverse mode of the structure, while the receive function involves a collection of modes typical of multimode operation. In this manner, the excellent spatial properties of single mode operation apply to the launch, while the large collection efficiency (numerical aperture) of a multimode fiber can be advantageously utilized at the receive end. While the aforementioned embodiments of the present invention may be the most useful for the problem at hand, they are by no means the only solutions encompassed by this invention.

Following are some additional features, advantages and uses of the single-fiber launch/receive system of the present invention:

The single-fiber launch/receive system utilizes fibers which enable efficient field repairs, where damaged fibers need only be re-cleaved or replaced as opposed to the expense and difficulty of repairing dual-fiber integrated optical devices.

The single-fiber launch/receive system is particularly well suited to be used in label-independent detection studies, where biological sensors are integrated into the bottom of each well in a 96, 384, or 1536-well plate. A traditional dual-fiber launch/receive system in this application could involve a crippling fiber management problem, while a single fiber solution reduces complexity by 50%.

It should be readily appreciated that many components and details associated with the interrogation systems described above are well known in the industry. Therefore, for clarity, the description provided above omitted those well known components and details that are not necessary to understand the present invention.

Although two embodiments of the present invention have been illustrated in the accompanying Drawings and described in the foregoing Detailed Description, it should be understood that the invention is not limited to the two embodiments disclosed, but is capable of numerous rearrangements, modifications and substitutions without departing from the spirit of the invention as set forth and defined by the following claims.

What is claimed is:

1. A single-fiber launch/receive system comprising a single fiber that interfaces with a biosensor wherein said single fiber has a fundamental mode therein which is excited and used to output a sensor input beam towards said biosensor, and wherein said single fiber has a collection of modes therein which are used to receive a sensor output beam from said biosensor.

2. The single-fiber launch/receive system of claim 1, wherein said single fiber is a multimode fiber.

3. The single-fiber launch/receive system of claim 2, wherein said multimode fiber is a graded-index multimode fiber.

4. The single-fiber launch/receive system of claim 2, wherein said fundamental mode is able to be excited because the multimode fiber is spliced to single mode fiber.

5. The single-fiber launch/receive system of claim 1, wherein said single fiber is a downjacketed singlemode fiber.

6. The single-fiber launch/receive system of claim 5, wherein said downjacketed singlemode fiber is a step-index, downjacketed singlemode fiber.

7. The single-fiber launch/receive system of claim 5, wherein said downjacketed singlemode fiber is made by surrounding a singlemode fiber with a fiber jacket that has a lower refractive index than a fiber cladding of the singlemode fiber.

8. The single-fiber launch/receive system of claim 7, wherein said fiber cladding is used to receive the sensor output beam from said biosensor.

9. The single-fiber launch/receive system of claim 1, further comprising a beam shaping optic located between said single fiber and said biosensor.

10. The single-fiber launch/receive system of claim 1, wherein said sensor input beam is not co-linear with said sensor output beam.

11. An interrogation system comprising:
a light source;
a light detector;
a single-fiber launch/receive system which uses a single fiber to output a sensor input beam to a biosensor when said light source excites a fundamental mode in the single fiber;

said single-fiber launch/receive system also uses the single fiber to receive a sensor output beam from the biosensor when a plurality of modes within the single fiber collects the sensor output beam which is then passed through the single fiber and directed to said light detector; and a computer/electrical hardware to analyze said sensor output beam received by said light detector to determine whether or not there was a bio-chemical interaction on said biosensor.

12. The interrogation system of claim 11, further comprising a coupler located between said single-fiber launch/receive system and both of said light source and said light detector.

13. The interrogation system of claim 11, wherein said single fiber is a multimode fiber and wherein the fundamental mode of said multimode fiber is excited by the light source by maximizing a spatial overlap of an output beam from the light source with the fundamental mode of the multimode fiber.

14. The interrogation system of claim 11, wherein said single fiber is a multimode fiber and wherein the fundamental mode of said multimode fiber is excited by splicing one end of a single mode fiber to said multimode fiber and directing an output beam from the light source into another end of the single mode fiber.

15. The interrogation system of claim 11, wherein said single fiber is a downjacketed singlemode fiber that was made by surrounding a singlemode fiber with a fiber coating jacket that has a lower index than a fiber cladding of the singlemode fiber.

16. The interrogation system of claim 11, further comprising a beam shaping optic located between said single-fiber launch/receive system and said biosensor.

17. The interrogation system of claim 11, wherein a plurality of said single-fiber launch/receive systems are used to interface with a plurality of said biosensors located in a microplate.

18. A method for interrogating a biosensor, said method comprising the steps of:
using a light source to output a sensor input beam into a single fiber which uses a fundamental mode to output said sensor input beam towards said biosensor;
using a light detector to receive a sensor output beam from said single fiber which uses a plurality of modes to receive said sensor output beam from said biosensor; and
using a computer/electrical hardware to analyze said sensor output beam received by said light detector to determine whether or not there was a bio-chemical interaction on said biosensor.

19. The method of claim 18, wherein said single fiber is a multimode fiber.

20. The method of claim 19, wherein said multimode fiber is a graded-index multimode fiber.

21. The method of claim 19, wherein said multimode fiber has the fundamental mode therein excited by the light source by maximizing a spatial overlap of the sensor input beam from the light source with the fundamental mode of the multimode fiber.

22. The method of claim 19, wherein said multimode fiber has the fundamental mode therein excited by splicing one end of a single mode fiber to said multimode fiber and directing the sensor input beam from the light source into another end of the single mode fiber.

23. The method of claim 18, wherein said single fiber is a downjaeketed singlemode fiber.

24. The method of claim 23, wherein said downjacketed singlemode fiber is made by surrounding a singlemode fiber with a fiber coating jacket that has a lower index than a fiber cladding of the singlemode fiber.

25. The method of claim 18, wherein said single fiber is associated with a concentric single-fiber launch/receive system.

26. An interrogation system comprising:
a light source;
a light detector;
a single-fiber launch/receive system including:
a singlemode fiber which receives a sensor input beani from said light source;
a first multimode fiber, spliced to said singlemode fiber, which has a fundamental mode therein that is excited by receiving the sensor input beam from said singlemode fiber;
a coupler which couples said first multimode fiber to a second multimode fiber which has a fundamental mode therein excited and used to output the sensor input beani towards a biosensor;
said second multimode fiber also has a collection of modes therein which are used to receive a sensor output beam from said biosensor; and
said coupler further couples said second multimode fiber to a third multimode fiber which has a collection of modes therein which direct the sensor output beam towards said light detector; and
a computer/electrical hardware to analyze said sensor output beam which is received by said light detector to determine whether or not there was a bio-chemical interaction on said biosensor.

27. An interrogation system comprising:
a light source;
a light detector;
a single-fiber launch/receive system including:
a singlemode fiber which receives a sensor input beam from said light source;
a first downjacketed singlemode fiber, spliced to said single mode fiber, which has a fundamental mode therein that is excited by receiving the sensor input beam from said single mode fiber;
a coupler which couples said first downjacketed singlemode fiber to a second downjacketed singlemode fiber which has a fundamental mode therein excited and used to output the sensor input beam towards a biosensor;
said second downjacketed singlemode fiber also has a fiber cladding which is used to receive a sensor output beam from said biosensor; and
said coupler further couples said second downjacketed singlemode fiber to a third downjacketed singlemode fiber which has a fiber cladding that directs the sensor output beam towards said light detector; and
a computer/electrical hardware to analyze said sensor output beam which is received by said light detector to determine whether or not there was a bio-chemical interaction on said biosensor.

* * * * *